(12) United States Patent
Yao et al.

(10) Patent No.: US 8,562,917 B2
(45) Date of Patent: Oct. 22, 2013

(54) ANALYTE METER SLEEVES AND METHODS

(75) Inventors: Raymond Yao, Ossining, NY (US);
Elgin Meike Toepfer, Roesrath (DE);
Jan Oliver Seyberth, Chicago, IL (US)

(73) Assignee: Bayer Healthcare LLC, Tarrytown, NY (US)

( * ) Notice: Subject to any disclaimer, the term of this patent is extended or adjusted under 35 U.S.C. 154(b) by 424 days.

(21) Appl. No.: 12/389,223

(22) Filed: Feb. 19, 2009

(65) Prior Publication Data
US 2010/0047126 A1  Feb. 25, 2010

Related U.S. Application Data

(60) Provisional application No. 61/090,502, filed on Aug. 20, 2008.

(51) Int. Cl.
*G01N 21/75* (2006.01)

(52) U.S. Cl.
USPC .......................................................... 422/410

(58) Field of Classification Search
USPC ............... 422/58, 61, 410; 702/19, 22, 25;
53/460, 464; D09/711; D24/108, 130,
D24/133, 216; 435/14, 287.1, 287.7, 288.7;
600/365, 583; 206/216, 370, 569
See application file for complete search history.

(56) References Cited

U.S. PATENT DOCUMENTS

| | | | | |
|---|---|---|---|---|
| 2,178,634 | A * | 11/1939 | Howenstine | 40/540 |
| 4,343,158 | A * | 8/1982 | Campbell | 62/372 |
| 5,279,294 | A * | 1/1994 | Anderson et al. | 600/322 |
| 5,865,032 | A * | 2/1999 | MacPherson et al. | 62/3.62 |
| 6,071,739 | A * | 6/2000 | Vadgama et al. | 435/287.9 |
| 6,095,682 | A * | 8/2000 | Hollander et al. | 374/121 |
| 2003/0038047 | A1 | 2/2003 | Sleva et al. | |
| 2005/0240119 | A1* | 10/2005 | Draudt et al. | 600/583 |
| 2006/0040333 | A1* | 2/2006 | Zocchi | 435/14 |
| 2006/0293577 | A1* | 12/2006 | Morrison et al. | 600/365 |
| 2008/0145272 | A1* | 6/2008 | Feaster et al. | 422/58 |

FOREIGN PATENT DOCUMENTS

| | | |
|---|---|---|
| DE | 3409706 A1 * | 7/1985 |
| DE | 200006107 U1 | 8/2000 |
| WO | WO 2005/102154 A2 | 11/2005 |
| WO | WO 2006/065702 A1 | 6/2006 |
| WO | WO 2006/121884 A1 | 11/2006 |
| WO | WO 2010/021761 | 2/2010 |
| WO | WO 2010-096054 | 8/2010 |

OTHER PUBLICATIONS

International Search Report and Written Opinion of International Application No. PCT/US2009/034589 dated May 26, 2009.
International Preliminary Report on Patentability and Written Opinion of International Application No. PCT/US2009/034589 dated Mar. 3, 2011.

* cited by examiner

*Primary Examiner* — Lore Jarrett
(74) *Attorney, Agent, or Firm* — Dugan & Dugan, PC

(57) ABSTRACT

In some aspects, an analyte meter sleeve is provided for storing an analyte meter (e.g., a blood glucose meter or insulin pump) and a lancet device. The sleeve includes a first sleeve member adapted to receive the analyte meter and a second member affixed to the sleeve and adapted to receive the lancet device. The first sleeve member may have a window adapted to allow viewing of a meter display. Numerous other aspects are provided.

2 Claims, 5 Drawing Sheets

ANALYTE METER SLEEVES AND METHODS

RELATED APPLICATIONS

The present application claims priority to U.S. Provisional Patent Application No. 61/090,502, filed Aug. 20, 2008, and entitled "BLOOD GLUCOSE METER SLEEVES", which is hereby incorporated herein by reference in its entirety for all purposes.

FIELD OF THE INVENTION

The present invention relates to analyte monitoring and/or control, and more particularly to sleeves for analyte meters used in analyte monitoring and/or control.

BACKGROUND OF THE INVENTION

The monitoring of analyte concentration levels in a biofluid (e.g., blood) may be an important part of health diagnostics. For example, analyte meters and accompanying sensors (sometimes referred to as "test strips") may be employed for the monitoring of a patient's blood glucose level as part of diabetes treatment and care. In blood glucose monitoring, for example, the patient may carry and use an analyte meter (e.g., a blood glucose meter) for providing a digital readout of a user's blood glucose level, and a portable lancet device for attaining a blood sample. The meter may be an Ascensia® BREEZE® 2 Blood Glucose Meter available from Bayer Healthcare, for example.

The lancet device may be a spring-loaded, trigger-releasable device which receives a single use, disposable lancet. For example, the lancet device may be an Ascensia® MICROLET® Lancet Device available from Bayer Healthcare. In use, the user may release the lancet device such that it may prick the user's body part (e.g., finger) to produce the droplet of blood. That blood droplet may then be transferred to a test strip which interfaces with, and may be received within a port in, the blood glucose meter.

Given that the users of such analyte meters and lancet devices need to carry such devices with them for blood analyte monitoring, there is a need for improved methods and apparatus for storing and carrying such devices.

SUMMARY OF THE INVENTION

In a first aspect, the present invention provides a blood glucose meter sleeve including a first sleeve member including a front panel and a back panel forming a first pocket adapted to receive an analyte meter, the front panel having a window allowing viewing and access to a meter display and one or more meter buttons, and an opening in a rear of the first pocket adapted to allow access to a port formed in the analyte meter; and a second sleeve member forming a second pocket proximate to the back panel, the second pocket adapted to receive a lancet device.

In another aspect, the present invention provides an analyte meter sleeve including a first sleeve member forming a pocket adapted to receive an analyte meter, the first sleeve member having a window adapted to allow viewing of a meter display of the analyte meter; and a second member affixed to the first sleeve member forming a retainer adapted to secure a lancet device to the first sleeve member.

In another aspect, the present invention provides a method of using an analyte meter sleeve including mounting an analyte meter in a first sleeve member; and mounting a lancet device in a second member affixed to the first sleeve member.

Other features and aspects of the present invention will become more fully apparent from the following detailed description, the appended claims and the accompanying drawings.

DETAILED DESCRIPTION

Because the user may desire to carry an analyte meter (e.g., a blood glucose meter) and the associated lancet device on their person at all times, and such devices may be easily misplaced from each other or lost, it may be desirable to provide an apparatus that would provide for carrying such devices and which may allow for ready access to the analyte meter and lancet device. In this manner, the processes of sample collection and analyte testing (e.g., blood glucose testing) may be readily performed and instances of misplacement of the devices may be reduced or eliminated.

Accordingly, in a first aspect of the present invention an analyte meter sleeve (e.g., a blood glucose meter sleeve) is provided. In one or more embodiments, the analyte meter sleeve may include a first sleeve member forming a pocket which is adapted to receive an analyte meter (e.g., a blood glucose meter), and a second member affixed to the first meter sleeve which is adapted to receive and secure a lancet device. The analyte meter sleeve is adapted for use with any type of analyte meter used for testing and/or control of an analyte, such as meters for testing glucose, hemoglobin A1c, lipids such as LDL, HDL and triglycerides, lactate, keytone, and other analytes. The term "analyte meter," as used herein, includes a blood analyte meter, an insulin pump, a controller for an insulin delivery system, a patch pump, a glucose meter, or other like metering devices.

The first sleeve member may include a window allowing viewing and access to a meter display of the analyte meter and one or more meter buttons thereof. Additionally, another opening may be provided in the first sleeve, such as in a rear of the pocket of the first sleeve member, which may be adapted to allow access to a sensor port formed which may be in the analyte meter. The sensor port is adapted to receive an analyte sensor (e.g., a sensor strip).

These and other embodiments of the analyte meter sleeve of the present invention are described below with reference to FIGS. 1-7.

Figure 1:
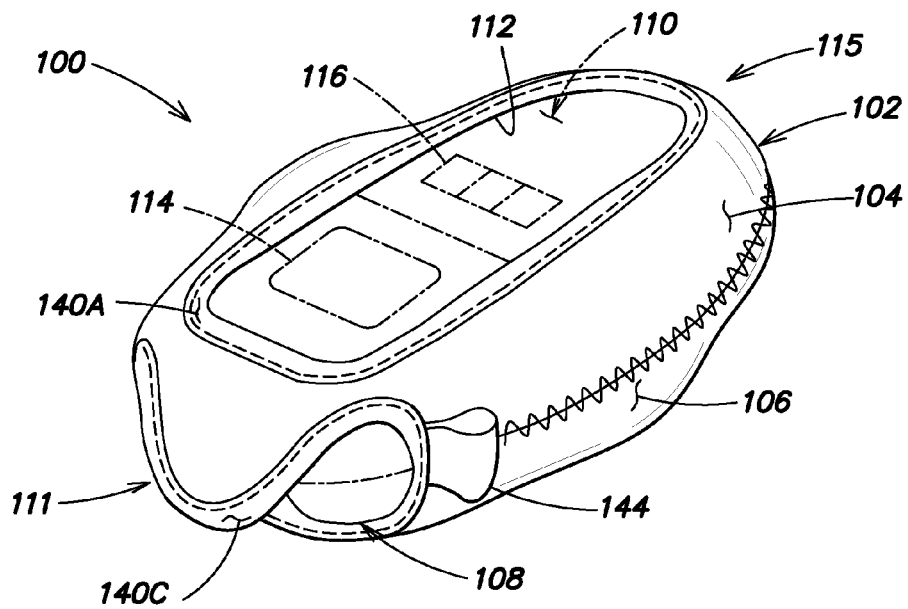
FIG. 1 is a front perspective view of an exemplary embodiment of an analyte meter sleeve provided according to the present invention.
Figure 2:
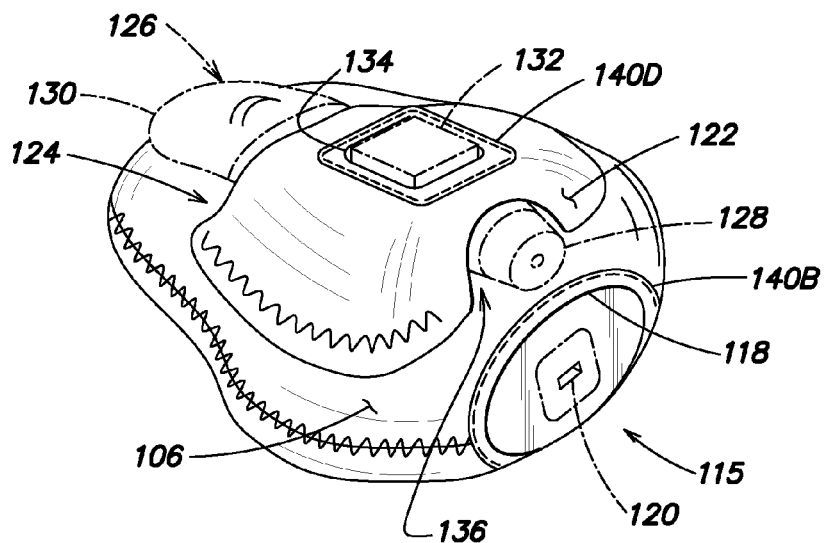
FIG. 2 is a back perspective view of the exemplary embodiment of the analyte meter sleeve of FIG. 1.

FIGS. 1-2 are perspective views of an exemplary embodiment of an analyte meter sleeve 100 (e.g., a blood analyte meter sleeve) provided according to the present invention which illustrate a front perspective view (FIG. 1) and a back perspective view (FIG. 2) of the meter sleeve 100. The meter sleeve 100 may include a first sleeve member 102 which may include a front panel 104 and a back panel 106. Together, the panels 104, 106 may form a first pocket 108 which is adapted to receive an analyte meter 110 (e.g., a blood analyte meter) at a first end 111 thereof. The panels 104, 106 may be stitched together by thread, for example. However, the first pocket 108 may be of any shape which forms a pocket that is adapted to receive and secure the analyte meter 110. Optionally, the first sleeve member 102 may be made of a one-piece construction, for example, which may be sewn together along one edge only.

In some embodiments, the front panel 104 may have a window 112 which may allow viewing of a display 114 and may also allow access to one or more meter buttons 116. The window 112 may be of any shape practical, and may be a simple cutout, for example. Optionally, the window may include a plastic protector cover over the display 114, for example. In one embodiment, separate windows may be provided for the display 114 and for the meter buttons 116. Further, the meter sleeve 100 may include an opening 118 therein. For example, the opening 118 may be positioned in a rear of the first pocket 108 at a second end 115 of the meter sleeve 100. The opening 118 may be circular, oval, race track shaped, square, rectangular, etc., for example. The opening may be adapted to allow access to the meter, such as by a test strip port 120 formed in the analyte meter 110 (e.g., a blood glucose meter) which is adapted to receive a test strip (not shown). The opening 118 may be provided in the sleeve 100 at any position where the port 120 is located on the meter 110. The opening 118 may further be adapted to receive a delivery tube when the meter is an insulin pump, for example.

As depicted in FIG. 2, the back panel 106 of the first sleeve member 102 may have mounted on, or affixed to, a second member, such as a second sleeve member 122 which may form a second pocket 124 proximate the back panel 106. The second pocket 124 may be of any shape adapted to receive a lancet device 126. The lancet device 126 may be any device adapted to penetrate the skin of the user. For example, the lancet device 126 may be any device which accepts disposable lancets, such as a MICROLET® 2 lancing device, or a MICROLET® VACULANCE® lancing device available from Bayer Healthcare. Other lancet devices may be received in the second pocket, such as HDU PRESTIGE LITE TOUCH lancing device, LIFESCAN ONE TOUCH® PENLET® PLUS lancing device, ACCU-CHEK® SOFT TOUCH® lancet device, SOFTCLIX lancet device available from Roche Diagnostics Corp., IQA lancing device available from Invacare, for example. The lancet device 126 may include, for example, a cocking mechanism 130, and a release button (or trigger) 132 and may further include a removable cap 128. In the case where the analyte meter 110 is an insulin pump, for example, the second pocket 124 may be adapted to receive an insertion kit which may include a disposable insertion device, a cannula, and a tubing connection. Further, the second pocket 124 may receive a transmitter/sensor assembly for when the analyte meter 110 is adapted for continuous analyte monitoring wherein the lancet is attached to the sensor component.

The second member 122 may have any shape suitable for retaining and securing the lancet device 126, and may, in some embodiments, be integrally formed with the first sleeve member 102. In some embodiments, the second sleeve member 122 may include a release button opening 134 which may be adapted to be aligned with, and allow access to, the release button 132 of the lancet device 126. The release button opening 134 may have a size and shape approximating the shape of the button, but slightly larger, for example. Other sizes and shapes may be used. The lancet device 126 may be oriented in the sleeve 100 in any fashion relative to the meter 110, but when the lancet device receives disposable lancets, preferably the sharp end (end with removable cap 128) of the lancet device 126 may be oriented on the same end of the sleeve 100 as the port 120.

According to some embodiments, the second sleeve member 122 may include a cap opening 136 formed in an end of the second pocket 124 which may be adapted to allow access to the removable cap 128 of the lancet device 126. As such, the cap 128 may be removed and a new disposable lancet (not shown) installed without needing to remove the lancet device 126 from the second pocket 124. As can be seen in FIG. 2, the second sleeve member 122 may, in some embodiments, extend only so far towards the first end 111 so that a user may freely grasp and operate the cocking mechanism 130. In some configurations, the second sleeve member 122 may be formed from a sheet of material which is stitched to the back panel 106 of the first sleeve member 102 by thread stitches, for example. Other forms of attachment may be used, such as glue, zippers, buttons, magnets, or snaps.

In the depicted embodiment of FIGS. 1-2, the front and back panels 104, 106 and the second sleeve member 122 of the meter sleeve 100 may be manufactured from a laminated sheet of material. The sheet may include, for example, a layer of cloth fabric and a layer of flexible material. The flexible material may comprise a polymer, such as a layer of elastomeric foam material. Optionally, the panels 104, 106 and second sleeve member 122, may be formed from a cloth. In the depicted embodiment, the front panel 104 and back panel 106 may be stitched together (e.g., using thread) along at least one side and may be stitched together along both sides, for example. Other materials may be used to form the first and second sleeve members 102, 122.

As also shown in the depicted embodiment, the front panel 104 and the back panel 106 may each include a closure member (not shown) which may be adapted to be secured to each other at an entry to the first pocket 108. The closure members will be described more thoroughly with reference to FIGS. 4 and 5 below. Any suitable closure member may be used that retains the meter 110 in the first pocket 108.

Figure 3:
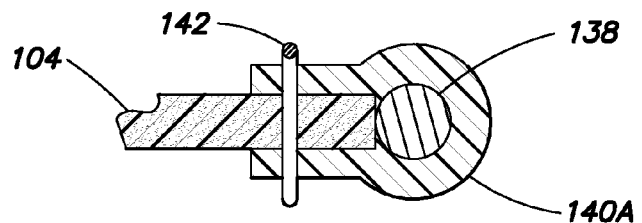
FIG. 3 is a partial cross-sectioned view illustrating detailed construction of a window of the exemplary embodiment of the analyte meter sleeve of FIGS. 1-2.

Now referring to FIGS. 1-3, in order to provide stability and avoid deformation of the sleeve 100, the window 112 may include a rigid member 138 (FIG. 3) providing reinforcement about a periphery of the window 112. The rigid member 138 may include a wire, such as a metal wire or any other deformable rigid stranded material (e.g., deformable plastic). The rigid member 138 may be provided adjacent to the window opening 112 in the front panel 104 and may be received in a binding 140A, provided around a periphery of the window 112. The rigid member 138 may be provided in segments or as one piece, and may be included all around the periphery of the window 112 or only at selected locations. The binding 140A may be a cloth or plastic material and may be folded over and stitched by thread 142 to the panel 104, for example. Similar bindings 140B, 140C, 140D, with or without a reinforcing rigid member, may be provided about the peripheries of the opening 118, around the entry into the first pocket 108, and/or about the release button window 132, respectively.

Optionally, the first sleeve member 102 may include an attachment member 144 which may be secured near the opening of the pocket 108 at the first end 111. For example, the attachment member 144 may be stitched into the first sleeve member 102 along with the binding 140C. The attachment member 144 may be provided anywhere on the body of the sleeve 100. Optionally, the sleeve 100 may include an attachment member 144 which may be a clip, belt loop strap or other connector, carrying handle or strap, carabineer, etc. The attachment member 144 may be adapted to attach the meter sleeve 100 to a user, for example.

Figure 4:
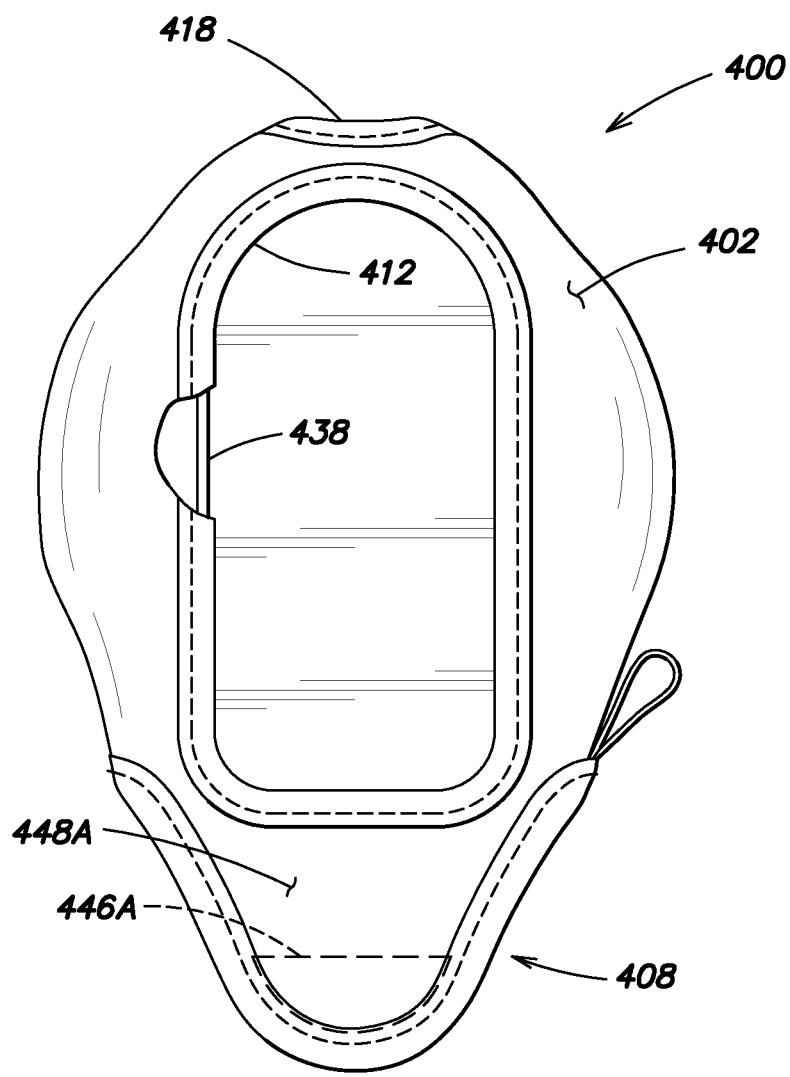
FIG. 4 is a front plan view of another exemplary embodiment of an analyte meter sleeve provided according to the present invention.
Figure 5:
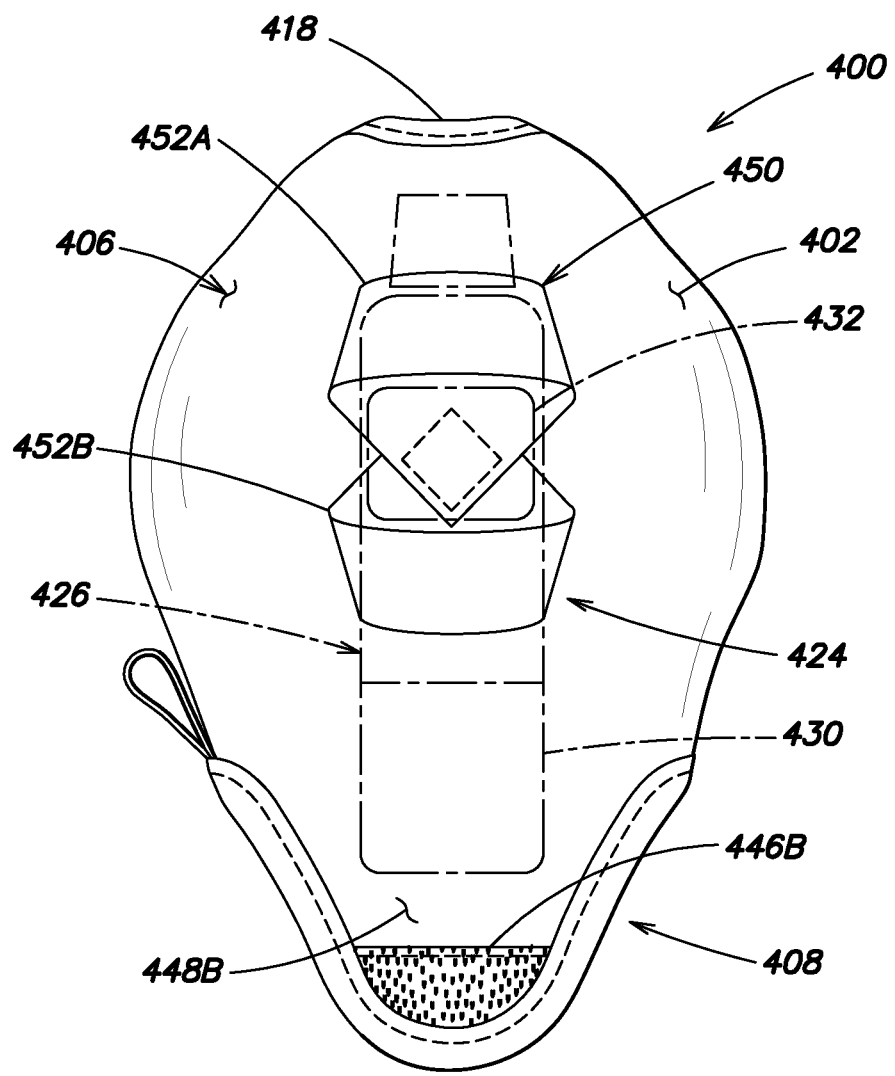
FIG. 5 is a back plan view of the exemplary embodiment of the analyte meter sleeve of FIG. 4.

Another embodiment of a meter sleeve 400 is illustrated in FIG. 4 with the meter removed for clarity. As in the previous embodiments, a first sleeve member 402 is provided, as are window 412 (including rigid member 438—shown in a cutout view), pocket 408 adapted to received the meter, and an opening 418 adapted to allow test strip or other access to a port of the meter. For example, when the analyte meter is an insulin pump, the opening 418 may be for a section of flexible tubing which extends from the meter to an infusion device (not shown). Clearly depicted in these views are closure members 446A (shown dotted), and 446B secured to the flaps 448A, 448B. The flaps 448A, 448B may be overlapped with each other as shown in FIG. 1, and the closure members 446A, 446B may then interface and contact with each other to provide closure. The closure members 446A, 446B may be one or more buttons, snaps, hooks, clasps, magnets, or other closure members. In the depicted embodiment, the closure may be provided by a VELCRO® closure including the closure members 446A, 446B wherein member 446A includes a strip with miniature hooks, and member 446B includes a strip with miniature loops, for example.

In the embodiment shown in FIG. 2, the second pocket 424 of may be formed from second member 450 such as a strap, for example. The second member 450 may be doubled over on itself thus forming several loops 452A, 452B which may receive the lancet device 426 (shown in phantom lines). The loops 452A, 452B may be made from an elastic fabric, for example. The second member 424 may be mounted on, and secured to, the panel 406 of the first sleeve member 402 by stitching or other suitable means such as glue, rivets, snaps, VELCRO® closure, etc. As illustrated, the second member 450 and loops 452A, 452B may be provided in a configuration such that a release button 432 (also shown in phantom) of the lancet device 426 may be adapted to be aligned (as installed) between the loops 452A, 452B. Further, a cocking mechanism 430 of the lancet device 426 may be readily cocked for use without removing the lancet device 426 from the second member 450. The second member 450 may be provided in a number of alternative forms. For example, the member 450 may include a series of elastic loops which are circular in cross section, a flexible U-shaped cradle, a pocket member, or retainer molded from a flexible polymer or elastomeric material. Other suitable configurations may be used depending on the size and shape of the lancet device 426.

Figure 6:
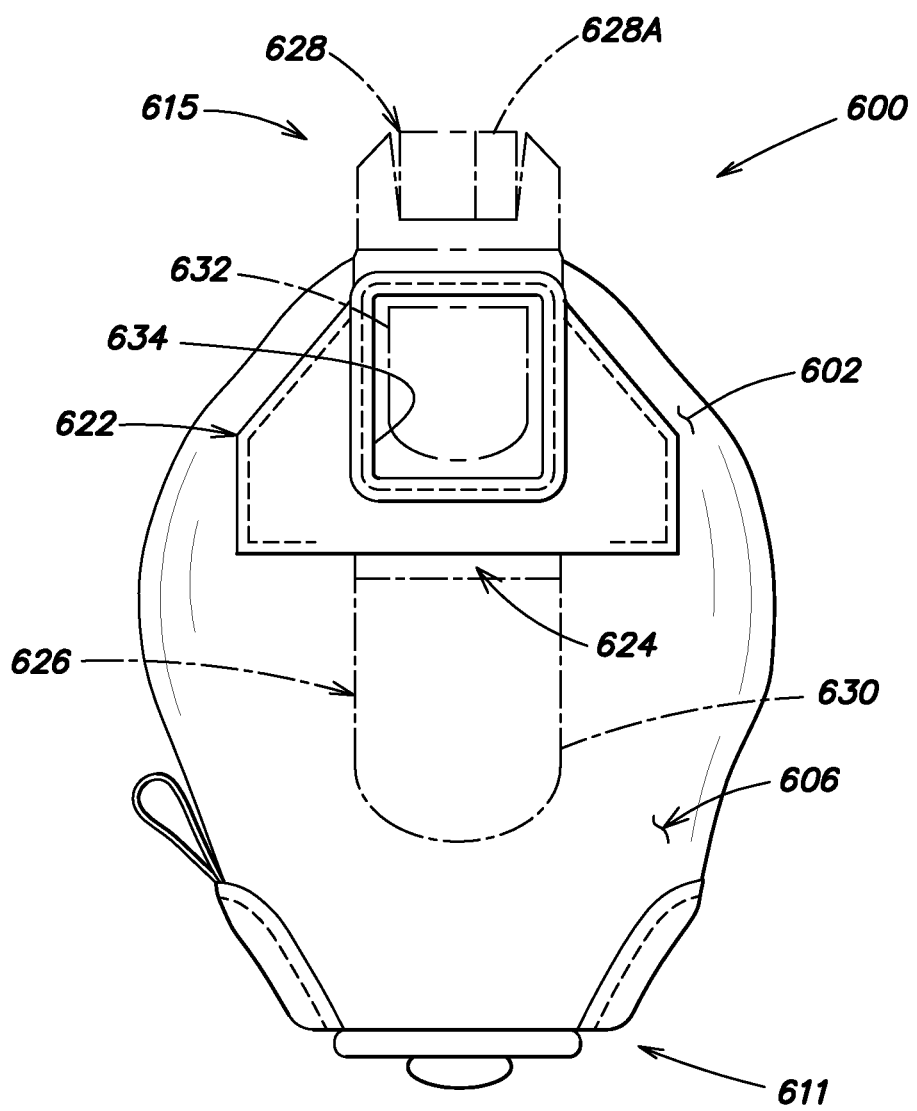
FIG. 6 is a back plan view of another exemplary embodiment of an analyte meter sleeve provided according to the present invention.
Figure 7:
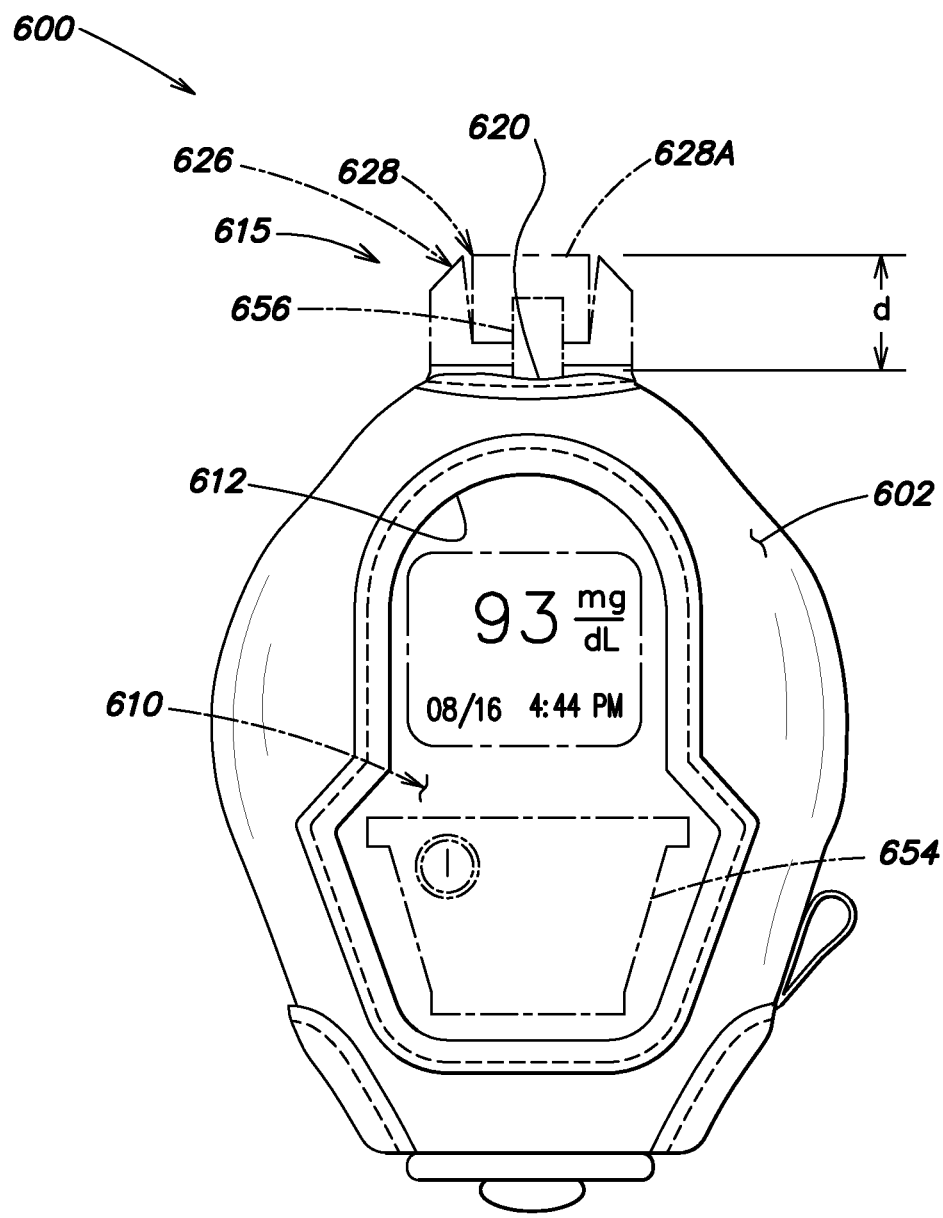
FIG. 7 is a front plan view of the exemplary embodiment of the analyte meter sleeve of FIG. 6.

Another exemplary embodiment of the meter sleeve 600 is illustrated in FIGS. 6 and 7. In this embodiment, the second member 622 (FIG. 6) is mounted to the first sleeve member 602 by stitches, for example. A second pocket 624 formed between the second member 622 and the back panel 606 may be oriented such that an outboard end 628A of a removable cap 628 of a lancet device 626 which is adapted to be received in the pocket 624 extends beyond an end (e.g., a test strip receiving end 615) of the first sleeve member 602 by a distance d. The distance d may be a sufficient distance such that the user may readily and easily access the cap 628. In this manner, the cap 628 may be readily removed by a user without having to remove the lancet device 626 from the pocket 624, such as when the user may be installing or removing a disposable lancet (not shown) received in the lancet device 626.

Additionally, the second member 622 may extend only so far towards the end 611 so that the cocking mechanism 630 of the lancet device 626 may be readily accessed and cocked by the user without having to remove the lancet device from the pocket 624. As in the previous embodiments, a release button opening 634 may be provided in the member 622. In the depicted embodiment, the meter 610 may include a pivoting panel 654 for accessing various meter features. In this case, the window 612 may be made sufficiently large in that area to allow access to the panel 654 of the meter 610. A test strip 656 is shown mounted in the port 620 of the meter 610. The closure members illustrated in this embodiment may include a snap, for example. Other closure members may be provided as previously described.

According to another aspect of the present invention, a method of using an analyte meter sleeve (e.g., a blood analyte meter sleeve) is provided, such as any of the meter sleeves described herein. The method may include mounting an analyte meter (e.g., a blood analyte meter) in a first sleeve member and mounting a lancet device in a second member affixed to the first sleeve member. The lancet device may be adapted to receive disposable lancets, for example. The method may further include steps of cocking the lancet device without removing the lancet device from the second member. The cocking may be provided by the user and may be accomplished by pulling or pushing a cocking mechanism, depending on the type used. The cocking mechanism may be any convention cocking mechanism provided on such lancet devices known in the art.

After cocking, the user may press a release button on the lancet device to actuate a lancet into the user's body part (e.g., finger). The release button may be part of the cocking mechanism in some instances. Following the release of the lancet mounted in the lancet device, the user may obtain a blood sample. This blood sample may then be transferred by the user to a test strip which may be received in a test port of the meter. In accordance with an aspect of the invention, the transfer may be accomplished without removing the meter from the first sleeve member.

In other embodiments, the analyte monitoring may be accomplished in a continuous fashion wherein the continuous analyte meter (e.g., a continuous blood glucose meter) is mounted in the first sleeve member and the lancet device mounted in the second member may be a remote transmitter/sensor system. In other embodiments, an insulin pump is mounted in the first sleeve member and the lancet device may be an insulin delivery device or insertion kit, for example.

The foregoing description discloses only exemplary embodiments of the invention. Modifications of the above disclosed analyte meter sleeves which fall within the scope of the invention will be readily apparent to those of ordinary skill in the art. Accordingly, while the present invention has been disclosed in connection with exemplary embodiments thereof, it should be understood that other embodiments may fall within the spirit and scope of the invention, as defined by the following claims.

The invention claimed is:

1. A method of using an analyte meter sleeve, comprising:
mounting an analyte meter having a test strip port in a first sleeve member comprising a cloth, wherein the first sleeve member surrounds a housing of the analyte meter; and
mounting a lancet device in a second member affixed to an exterior surface of the first sleeve member such that a sharp end of the lancet device is oriented on a same end of the analyte meter sleeve as the test strip port.

2. The method of claim 1 further comprising:
cocking the lancet device without removing the lancet device from the second member; and
pressing a release button on the lancet device.

* * * * *